United States Patent [19]
Yuhda et al.

[11] Patent Number: 6,063,832
[45] Date of Patent: *May 16, 2000

[54] METHOD OF SETTING A DENTAL CEMENT COMPOSITION

[75] Inventors: Sadayuki Yuhda; Hiroshi Kameda, both of Otawara, Japan

[73] Assignee: Sankin Kogyo Kabushiki Kaisha, Otawara, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/730,288

[22] Filed: Oct. 11, 1996

[30] Foreign Application Priority Data

Mar. 25, 1996 [JP] Japan ..................... 8-068675

[51] Int. Cl.$^7$ .............. A61K 6/083; C08K 3/22
[52] U.S. Cl. .............. 523/116; 523/113; 524/444; 524/450; 524/533; 524/547; 524/556; 433/228.1
[58] Field of Search ............... 523/116, 113; 524/556, 444, 450, 547, 533

[56] References Cited

U.S. PATENT DOCUMENTS

| | | |
|---|---|---|
| 4,832,745 | 5/1989 | Antonucci . |
| 4,872,936 | 10/1989 | Engelbrecht ............... 523/116 |
| 5,063,257 | 11/1991 | Akahane et al. ............ 523/116 |
| 5,130,347 | 7/1992 | Mitra ....................... 523/116 |
| 5,151,453 | 9/1992 | Ibsen et al. ................ 523/115 |
| 5,306,338 | 4/1994 | Tsunekawa ................ 523/116 |
| 5,367,002 | 11/1994 | Huang et al. .............. 523/115 |
| 5,861,445 | 1/1999 | Xu et al. ................... 523/115 |

FOREIGN PATENT DOCUMENTS

| | | |
|---|---|---|
| 0 554 890 A1 | 8/1993 | European Pat. Off. . |
| 0 391 619 A2 | 10/1999 | European Pat. Off. . |
| 54-21858 | 8/1979 | Japan . |
| 57-2210 | 1/1982 | Japan . |
| 6-27047 | 4/1994 | Japan . |
| 6-27049 | 4/1994 | Japan . |

OTHER PUBLICATIONS

John Nicholson et al., The Development of Modified Glass–ionomer Cements for Dentistry, Trends in Polymer Science, vol. 2, No. 8, Aug. 1, 1994.

*Primary Examiner*—Andrew E. C. Merriam
*Attorney, Agent, or Firm*—Fish & Richardson P.C.

[57] ABSTRACT

A practically non-aqueous dental cement composition is disclosed and the dental cement composition comprises a polymer or co-polymer having an $\alpha,\beta$-unsaturated carboxylic acid as an essential component of a main monomer; and an inorganic powder capable of forming a metal chelate in the presence of water characterized in that the polymer or co-polymer exists as a solution in a polymerizable monomer that can dissolve the polymer or co-polymer. This provides a dental composition which has not only the advantages of the conventional glass ionomer cement but also a higher setting rate and more desirable physical properties of the setting product and is excellent also in durability, by eliminating the disadvantages in the setting rate and physical properties of the set cement.

14 Claims, No Drawings

METHOD OF SETTING A DENTAL CEMENT COMPOSITION

BACKGROUND OF THE INVENTION

This invention relates to the dental cement composition, and in more detail, this invention relates to dental cement compositions which, in contrast to the conventional aqueous dental cement compositions, are practically non-aqueous, being excellent in initial adhesion, cementing, and filling ability to the tooth, and showing excellent strength and water-resistance after setting.

Among many kinds of dental cement now available to us, the most frequently used are the phosphate cement based on the reaction between zinc oxide and phosphoric acid, the polycarboxylate cement based on the reaction between zinc oxide and polycarboxylic acid, the zinc oxide-eugenol cement based on the reaction between zinc oxide and eugenol, and the glass-ionomer cement based on the reaction between fluoroaluminosilicate glass powder and polycarboxylic acid, among which the glass ionomer cement is frequently used as the most preferable cement.

Each of these dental cement has advantages and disadvantages, and none of them is ideal. For example, the zinc phosphate cement has poor adhesion to the tooth and shows irritability due to phosphoric acid at the beginning of setting; the polycarboxylate cement has poor final strength of the set cement; the eugenol cement is poor in the strength and in the intraoral durability, so that it is used only for temporary sealing or temporary cementing, and the irritability specific to eugenol is a disadvantage.

In contrast to these cement, the glass ionomer cement is excellent in biocompatibility, adhesion to the tooth, intraoral durability in the mouth, etc., and in addition, it is excellent from the esthetic viewpoint because it is translucent. Based on these characteristics, the glass ionomer cement is widely used for cementing of inlay, crown, etc., filling of caries cavities, lining, preventive filling of pits and fissures, etc.

The most undesirable characteristic of the glass ionomer cement is that the setting reaction is inhibited when the cement comes in contact with water such as saliva in the initial stage immediately after mixing, which may finally result in deteriorated physical properties. That is, although the glass ionomer cement begins to set in the presence of water based on the chelate formation between a polycarboxylic acid and a polyvalent metal derived from fluoroaluminosilicate glass, that is, the setting reaction requires water for release of metal ions, water present in the setting system or the setting cement is undesirable for increase of setting rate or of initial strength. In addition, when the setting reaction proceeds in the presence of water, the surface of the setting cement becomes white-clouded, which is undesirable from the esthetic viewpoint.

Various techniques to eliminate these disadvantages of the glass ionomer cement have been developed; for example, addition of an organic chelating agent to increase the initial setting rate (Japanese Patent Publication No.21858/1979), addition of a fluoro-complex to increase the initial setting rate (Japanese Unexamined Patent Publication No.2210/1982), combination of a polymerizable unsaturated compound and a polymerization catalyst to increase the initial setting rate (Japanese Patent Publication No.27049/1994), etc. have been proposed and seem to be effective in their own way.

However, usual dental cement including the above-mentioned glass ionomer cement are always used in the form of an aqueous paste for acceleration of the metal cross linking reaction between the polyvalent metal in the cement powder and a polycarboxylic acid. Therefore, as mentioned above, the presence of water exerts not a small undesirable influence on the setting rate and the initial strength, so that the quality-improving effect is smaller than expected.

SUMMARY OF THE INVENTION

This invention was made by taking the above-mentioned circumstances into consideration, and the object of the invention is to provide a dental cement composition which has not only the advantages of the conventional glass ionomer cement but also a higher setting rate and a higher initial strength as the result of elimination of the disadvantages of the conventional and is excellent in durability.

A dental cement composition according to this invention comprises a polymer or co-polymer having an $\alpha,\beta$-unsaturated carboxylic acid as an essential component of a. main monomer and an inorganic powder capable of forming a metal chelate in the presence of water and wherein the polymer or co-polymer exists as a solution in a polymerizable monomer that can dissolve the polymer or co-polymer.

For practical use, the dental cement composition of this invention may be in the form of a paste in which the above-mentioned metal chelate-forming inorganic powder is dispersed in the solution of the above-mentioned carboxyl group-containing polymer in a polymerizable monomer, and it is more desirable that a cement powder containing the above-mentioned inorganic powder and a solution of the above-mentioned carboxyl group-containing polymer in a polymerizable monomer are separately prepared beforehand, and mixed immediately before use.

The $\alpha,\beta$-unsaturated carboxylic acid constituting the above-mentioned carboxyl group-containing polymer is desirably (meth)acrylic acid, and the polymerizable monomer which is used in combination of the said acid is desirably a hydroxyl group-containing alkyl (meth)acrylate, such as hydroxymethyl (meth)acrylate, hydroxyethyl (meth)acrylate, hydroxypropyl (meth)acrylate, hydroxybutyl (meth)acrylate, and hydroxyhexyl (meth)acrylate, or mono- or di-glycerol ester of (meth)acrylic acid, or mono-, di-, or tri-pentaery thritol ester of (meth)acrylic acid, among which hydroxy-methyl (meth)acrylate and hydroxyethyl (meth) acrylate are particularly desirable. The molecular weight of the above-mentioned carboxyl group-containing polymer used in this invention is desirably in the range of 2,000 to 50,000 as expressed in the weight average molecular weight.

Representative metal chelate-forming inorganic powders used as described above may be one or two or more compounds selected from oxides, hydroxides, carbonates, phosphates, and silicates of polyvalent metals, among which polyvalent metal ion-exuding glass, a silicate, particularly fluoroaluminosilicate glass, which releases fluorine and therefore is effective in strengthening and protection of teeth, is more desirable.

The dental cement composition of this invention may be allowed to initiate the polymerization of the above-mentioned polymerizable monomer by heating in the initial stage of the reaction, and it is more desirable and very effective to include a polymerization initiator (radical polymerization initiators including the redox polymerization initiators and photosensitizers) for the polymerizable monomer as an additional component in the composition to make the composition subject to photosetting and to increase the setting reaction rate.

In this invention the polymerizable component essential for increase of the initial strength is a polymerizable monomer which can dissolve the above-mentioned carboxyl group-containing polymer, especially an alkyl (meth) acrylate containing a hydroxyl group in the molecule. In addition, it is also effective to include a phosphoric ester of (meth)acrylic acid, another (meth)acrylate and/or a carbamate, which can be co-polymerized with the above-mentioned polymerizable monomer, in the composition as an additional component, so that the initial setting reaction rate and the initial strength may be increased.

The inventors have made many researches in the attempt to make the best use of the advantageous properties of the dental cement compositions obtained with the above-mentioned prior art which ensures the strength of the setting product by employing a polyvalent metal compound as the metal chelate-forming inorganic powder and by utilizing the metal cross-linking with a carboxyl group-containing polymer, and to correct the defects in the setting rate and in the properties of the set cement.

As the result of our researches, we found that use of a polymerizable monomer is effective for increase of the initial setting rate and the initial strength, and that, when the said monomer is used as a reactive solvent for the carboxyl group-containing polymer so that the cement composition may be used as a non-aqueous paste, the problems such as insufficient initial strength due to water in the aqueous cement are solved successfully. Thus we have completed the invention.

Namely, the fundamental conception of the present invention consists in that the dental composition is practically a non-aqueous cement wherein a polymerizable monomer is used as a reactive solvent to dissolve a carboxyl group-containing polymer, and an inorganic powder is also included which forms a metal chelate in the presence of water. The invention intends to improve setting characteristics and the initial strength by polymerizing the above-mentioned polymerizable monomer by heat treatment of the composition, or desirably by use of a polymerization initiator as described below. Thus practically no water is included in the setting reaction system of the cement composition of this invention, and the polymerizable monomer serving as a solvent or a dispersion medium rapidly polymerizes in the initial stage of setting to be eliminated from the system. Therefore the composition of this invention shows remarkably higher initial setting rate and initial strength than the conventional aqueous cement.

As described above, practically no water is contained in the cement composition of this invention, and therefore a suspicion may be aroused that the polyvalent metal contained in the metal chelate-forming inorganic powder is not ionized and therefore the strength is not increased by the metal cross-linking with the carboxyl group-containing polymer. However, the dental cement used in the oral cavity for filling of the defect of teeth is always exposed to water contained in the saliva in the oral cavity, and therefore the water permeates the cement to ionize the polyvalent metal in the metal chelate-forming inorganic powder so that a metal bridge is formed with the carboxyl group-containing polymer. That is, in this invention, the initial setting reaction proceeds, practically in the absence of water, rapidly along with polymerization of the reactive solvent (a polymerizable monomer), and then with the aid of water which has permeated the cement in the oral cavity, the setting reaction based on the metal bridging proceeds; in this manner the invention is effective in improvement of the setting reaction rate and of the properties of the setting product, making sure of excellent durability.

In the following is illustrated each component of the dental cement composition of this invention in more detail.

The polymer or co-polymer comprising an $\alpha,\beta$-unsaturated carboxylic acid as the main monomer (a carboxyl group-containing polymer) is a polymer comprising a monomer as the main component which contains a carboxyl group and a polymerizable double bond in the molecule; the said monomer component is represented by acrylic acid, maleic acid, fumaric acid, itaconic acid, gluconic acid, aconitic acid, citraconic acid, mesaconic acid, crotonic acid, iso-crotonic acid, 3-butenoic acid, maleic anhydride, itaconic anhydride, and the like, among which acrylic acid is particularly desirable. These $\alpha,\beta$-unsaturated carboxylic acids may be used alone or in combination of two or more of them, but in this invention it is desirable that the proportion of the $\alpha,\beta$-unsaturated carboxylic acid unit in the carboxyl group-containing polymer is about 50 mole % or more, more desirably about 80 mole % or more.

The co-polymerizable monomer which can, if necessary, co-polymerize with the above-mentioned $\alpha,\beta$-unsaturated carboxylic acid is not specified, and represented by methyl (meth)acrylate, n-propyl (meth)acrylate, isopropyl (meth)acrylate, phenyl (meth)acrylate, benzyl (meth)acrylate, 2-ethylhexyl (meth)acrylate, n-butyl (meth)acrylate, isobutyl (meth)acrylate, decyl (meth)acrylate, lauryl (meth)acrylate, stearyl (meth)acrylate, glycidyl (meth)acrylate, glyceryl (meth)acrylate, diethylaminoethyl (meth)acrylate, (meth)acrylamide, vinyl acetate, styrene, $\alpha$-methylstyrene, 2,2-bis[(meth)acryloxypolyethoxyphenyl]propane (generally called 2.6 E in the field of dentistry), 2,2'-bis[4-(3-(meth)acryloyloxy-2-hydroxypropoxy)phenyl]propane (generally called Bis-GMA), (meth)acrylonitrile, and various substitution products and derivatives thereof.

The molecular weight of the carboxyl group-containing polymer is desirably in the range of 2,000 to 50,000 as expressed in the weight average molecular weight, more desirably in the range of 5,000 to 35,000; if the molecular weight is below 2,000, the set cement may be insufficient in the strength, and if the molecular weight is over 50,000, the solubility in the polymerizable monomer used as a reactive solvent may be decreased, offsetting the advantages of this invention.

The polymerizable monomer used as the solvent for the said carboxyl group-containing polymer may be any as far as it can dissolve the carboxyl group-containing polymer, being desirably a monomer of the (meth)acrylate series containing a hydroxyl group in the molecule; the most effective solvent for a polymer or co-polymer of which main monomer component is (meth)acrylic acid is a hydroxyalkyl (meth)acrylate.

The metal chelate-forming inorganic powder is a polyvalent metal compound which can form a metal cross-linking with the carboxyl group in the above-mentioned carboxyl group-containing polymer, and exemplified by oxides of polyvalent metals known as the so-called cement powder in the field of dental cement, such as zinc oxide, strontium oxide, magnesium oxide, calcium oxide, aluminum oxide, and the like; hydroxides such as zinc hydroxide, calcium hydroxide, aluminum hydroxide, and the like; carbonates such as zinc carbonate, calcium carbonate, aluminum carbonate, strontium carbonate, and the like; phosphates such as calcium phosphate, zinc phosphate, aluminum phosphate, and the like; silicates such as aluminum silicate, calcium silicate, aluminum borosilicate, and the like, among which a polyvalent metal-exuding glass, a silicate, such as aluminosilicate glass, is particularly desirable, and the fluoride-ion-releasing aluminofluorosilicate glass is recommended as a particularly desirable metal chelate-forming inorganic powder. The said aluminofluorosilicate glass can be produced according to the method disclosed in the U.S. Pat. No. 4,775,592, No. 3,814,717, No. 4,360,605, and No. 4,376,835.

The above-mentioned inorganic powder is desirably composed of relatively small particles of 10 μm or less in the mean particle diameter. With the particles of a smaller diameter, more homogeneous and dense cement paste is obtained, which is favorable for filling, etc., and in addition, the surface area becomes so large that the setting characteristics become more desirable and the set cement becomes more homogeneous.

The cement composition of this invention contains the above-mentioned carboxyl group-containing polymer, a polymerizable monomer as a solvent for the polymer, and a metal chelate-forming inorganic powder as the essential components, of which desirable composition is 2 to 30 weight %, more desirably 5 to 20 weight %, of the carboxyl group-containing polymer, 5 to 40 weight %, more desirably 10 to 30 weight %, of the polymerizable monomer, and 30 to 90 weight %, more desirably 50 to 80 weight %, of the metal chelate-forming inorganic powder.

The cement composition may be set by heat, and for routine use it is desirable to utilize a known polymerization initiator that produces radicals, for example a peroxide such as BPO. It is a recent trend to allow to set under the light such as visible rays, and therefore it is desirable to add a photo-polymerization initiator to the said composition to render the composition susceptible to photo-setting. As the photo-polymerization initiator, are particularly desirable camphorquinone, benzil, biacetyl, 9,10-phenanthrenequinone, naphthoquinone, etc. which are highly photosensitizable, among which camphorquinone is the most desirable. Other desirable examples of the above-mentioned polymerization initiator are the redox initiators in combination with a small amount of a reducing agent, and the reducing agent used here is desirably of the tertiary amine series, such as N,N-dimethylamino-p-toluidine, butyl-diethanolamine, N,N-dimethylaminoethyl methacrylate, morpholinoethyl methacrylate, ethyl-p-(N,N-dimethylamino) benzoic acid, 2-methacryloxyethyl-p-(N,N-dimethylamino)benzoic acid, dimethylaminobenzoic acid, and the esters thereof.

It is also effective to use, in addition to the above-mentioned components, a polymerization accelerator such as aromatic sulfinic acids, sulfonyl compounds (e.g. sodium p-toluenesulfinate, sodium benzenesulfinate, etc.), sodium sulfite, potassium sulfite, etc.

The total amount of the additional components including the above-mentioned photopolymerization initiator, photo-sensitizer, reducing agent, etc. is desirably in the range of 0.2 to 5 weight %, more generally 0.5 to 2 weight %, of the total amount of the cement composition.

For the practice of this invention, it is also effective to add, in addition to the above-mentioned components, a phosphoric ester of (meth)acrylic acid, other (meth)acrylate, and carbamate that can co-polymerize with the above-mentioned monomer component, to improve the characteristics of the initial setting reaction and the properties of the setting product.

Phosphoric esters of (meth)acrylic acid used herein are exemplified by phosphate group-containing (meth)acrylate derivatives such as (meth)acryloxyethyl phosphate, (meth) acryloxypropyl phosphate, (meth)acryloxybutyl phosphate, (meth)acryloxypentyl phosphate, (meth)acryloxyhexyl phosphate, and the like, which are represented by the following general formula.

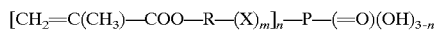

(wherein, R is a lower alkyl group, X is O, S, or NH, m is an integer of 0 or 1, and n is an integer of 1 or 2.)

Among the above-mentioned phosphoric esters, are particularly desirable pyrophosphoric esters of (meth)acrylic acid, especially tetra(meth)acryloxyethyl pyrophosphate, which can be produced for example by the following method.

A solution of 4 moles of 2-hydroxyethyl (meth)acrylate and 4 moles of triethylamine in anhydrous benzene is added dropwise to a solution of 1 mole of tetrachloropyrophosphoric acid in anhydrous benzene with vigorous stirring at −15° C., and the mixture was stirred at 0° C. for 2 hours and then at room temperature for 1 hour. The benzene phase is extracted, washed with the 5% aqueous hydrochloric acid solution, neutralized with the aqueous sodium carbonate solution, washed with water, separated, and dried with sodium sulfate. Then the benzene is evaporated off under reduced pressure, to give a colorless oily product of tetra (meth)acryloxyethyl pyrophosphate.

The other (meth)acrylate compounds that can co-polymerize with the above-mentioned polymerizable monomer are exemplified non-restrictively by methyl (meth)acrylate, n-propyl (meth)acrylate, isopropyl (meth) acrylate, phenyl (meth)acrylate, benzyl (meth)acrylate, 2-ethylhexyl (meth)acrylate, n-butyl (meth)acrylate, isobutyl (meth)acrylate, decyl (meth)acrylate, lauryl (meth) acrylate, stearyl (meth)acrylate, glycidyl (meth)acrylate, glyceryl (meth)acrylate, triethyleneglycol (meth)acrylate, diethylaminoethyl (meth)acrylate, 2,2-bis[(meth) acryloxyethoxyphenyl]propane, 2,2'-bis[4-(3-(meth) acryloyloxy-2-hydroxypropoxy)phenyl]propane, etc.

The carbamate compounds are exemplified by di-2-(meth)acryloxyethyl-hexamethylene dicarbamate, di-2-(meth)acryloxyethyl-trimethylhexamethylene dicarbamate, di- 2-(meth)acryloxyethyl-dimethylbenzene dicarbamate, di-2-(meth)acryloxyethyl-dimethylcyclohexane dicarbamate, methylenebis-2-(meth)acryloxyethyl-4-cyclohexyl dicarbamate, di-1-methyl-2-(meth) acryloxyethyl-hexamethylene dicarbamate, di-1-methyl-2-(meth)acryloxyethyl-trimethylhexamethylene dicarbamate, di-1-methyl-2-(meth)acryloxyethyl-dimethylbenzenetrimethylhexamethylene dicarbamate, di-1-methyl-2-(meth)acryloxyethyl-dimethylbenzene dicarbamate, di-1-methyl-2-(meth)acryloxyethyl-dimethylcyclohexane dicarbamate, methylenebis-1-methyl-2-(meth)acryloxyethyl-4-cyclohexyl carbamate, di-1-chloromethyl-2-(meth)acryloxyethyl-hexamethylene dicarbamate, di-1-chloromethyl-2-(meth)acryloxyethyl-hexamethylene dicarbamate, and the like.

These phosphoric ester compounds, (meth)acrylate compounds, and carbamate compounds may be used in a relatively great variation of combination as far as they do not exert adverse effects on the characteristics of the above-mentioned polymerizable monomer. However, because, when used in excess, they may inhibit dissolution of the carboxyl group-containing polymer, it is desirable to use 60 or less parts of them per 100 parts of the above-mentioned polymerizable monomer by weight.

The dental cement composition of this invention contains the above-mentioned carboxyl group-containing polymer, a polymerizable monomer to dissolve the said polymer, a metal chelate-forming inorganic powder, and desirably also a polymerization initiator, and a phosphoric ester of (meth) acrylic acid, a (meth)acrylate and/or a carbamate. The composition may be used as a one-liquid type paste prepared as a homogeneous mixture of the components. Because polymerization may proceed during storage of the composition, especially of the one containing also a polymerization initiator, it is required to store in a cold, dark place. Therefore it is recommended that a liquid preparation of the solution of the carboxyl group-containing polymer in a polymerizable monomer, or the said solution containing also a phosphoric ester of (meth)acrylic acid, (meth)acrylate, carbamate, etc., and a powder preparation of a metal chelate-forming inorganic powder are prepared separately, and these are mixed immediately before use together with a polymerization initiator.

DETAILED DESCRIPTION OF THE PREFERRED EMBODIMENTS OF THE INVENTION

In the following this invention is illustrated in more concrete with Examples, which, however, do not limit the invention. Adequate modification is allowable as far as it is compatible with the object of this invention described above or below, and every such modification is included in the technical scope of this invention.

[Production of aluminofluorosilicate glass]

Silicon dioxide, aluminum phosphate, aluminum hydroxide, calcium carbonate, strontium carbonate, strontium nitrate, and aluminum fluoride were mixed at the ratios shown in Table 1, fused at 1350° C. in a platinum crucible, cooled rapidly, and pulverized in a ball mill. The resultant powder product was sieved through a 325-mesh sieve, to give aluminofluorosilicate glass powder (called glass powder hereinafter). To 100 g of this glass powder was added 50 g of the 4 weight % solution of γ-methacryloxypropyl trimethoxysilane in ethyl alcohol, and the mixture was stirred for 1 hour, dried, and heated at 110° C. for 30 minutes, to give a silane-treated glass powder which was used as the reactive inorganic powder in the Examples described below.

TABLE 1

| Raw material | parts by weight |
|---|---|
| silicon dioxide | 35.0 |
| aluminum phosphate | 7.0 |
| aluminum hydroxide | 9.0 |
| calcium carbonate | 10.5 |
| strontium carbonate | 21.5 |
| strontium nitrate | 5.0 |
| aluminum fluoride | 25.0 |

The test methods used in the Examples described below are:

[Compressive strength]

From the mixture of the composition described in each Example, were prepared test pieces of 4 mm in diameter and 5 mm in height for determination of the compressive strength, and immersed in purified water at 37° C. for 24 hours before determination of the compressive strength in a compression test machine.

[Water-leachable content]

From the mixture of the composition described in each Example, were prepared test pieces of 20 mm in diameter and 1.5 mm in thickness for determination of the water-leachable content, and the water leachable content was determined according to JIS T6603 (1994).

[Fluoride ion release]

From the mixture of the composition described in each Example, were prepared two test pieces of 20 mm in diameter and 1.5 mm in thickness for determination of the fluoride ion release, and immersed in 5 ml of the phosphate buffer at 37° C. for 24 hours. The concentration of fluoride ion released into the phosphate buffer was determined by using a fluoride ion electrode.

EXAMPLE 1

To 100 g of the above-mentioned silane-treated glass powder, was added 0.2 g of ethyl dimethylaminobenzoate (a reducing agent), and the mixture was mixed thoroughly to give a cement powder. Separately, 20 g of polyacrylic acid having an average molecular weight of 30,000 was dissolved in 80 g of 2-hydroxyethyl methacrylate (a polymerizable monomer), to which 0.4 g of camphorquinone (a photo-sensitizer) was dissolved homogeneously, to give a cement liquid. 1.0 g of this cement liquid was added to 4.0 g of the above-mentioned cement powder and kneaded for 30 seconds. The resultant mixture was molded into test pieces of suitable size for each test, and allowed to set with a visible rays polymerizer ("Suncure-light" of Sankin Kogyo Co.). The compressive strength, water-leachable content, and fluoride ion release of the test piece were determined.

EXAMPLE 2

To 100 g of the above-mentioned silane-treated glass powder, was added 0.2 g of ethyl dimethylaminobenzoate and 1.0 g of sodium p-toluenesulfinate (a polymerization accelerator), and the mixture was mixed to give a cement powder. Separately, 20 g of polyacrylic acid having an average molecular weight of 30,000 was dissolved in 80 g of 2-hydroxyethyl methacrylate, and in 40 g of this solution were dissolved homogeneously 20 g of tetramethacyloxyethyl pyrophosphate, 30 g of triethyleneglycol dimethacrylate, 10 g of dimethacryloxytrimethylhexane dicarbamate, and 0.4 g of phorquinone, to give a cement liquid. 1.0 g of this cement liquid was added to 4.0 g of the above-mentioned cement powder and kneaded for 30 seconds. The resultant mixture was molded into test pieces of suitable size for each test, and allowed to set with a visible rays polymerizer ("Suncurelight" of Sankin Kogyo Co.). The compressive strength, water-leachable content, and fluoride ion release of the specimen were determined.

EXAMPLE 3

In 50 g of a solution prepared by dissolving 20 g of polyacrylic acid having an average molecular weight of 30,000 in 80 g of 2-hydroxyethyl methacrylate, were dissolved by stirring in a dark room 40 g of triethyleneglycol dimethacrylate, 10 g of dimethacryloxytrimethylhexane dicarbamate, 0.5 g of camphorquinone, and 0.5 g of ethyl dimethylaminobenzoiate, to give a liquid mixture. 10 g of this liquid mixture was mixed by kneading with 40 g of silane-treated glass powder, to give a paste. This paste was molded into test pieces suitable in size for each test, as described in the Example 1, and the compressive strength, water-leachable content, and fluoride ion release were determined.

EXAMPLE 4

In 20 g of a solution prepared by dissolving 20 g of polyacrylic acid having an average molecular weight of 30,000 in 80 g of 2-hydroxyethyl methacrylate, were dissolved by stirring in a dark room 10 g of triethyleneglycol dimethacrylate, 5 g of 2,2'-bis[4-(3-methacryloxy-2-hydroxypropoxy)phenyl]propane (Bis-GMA), 35 g of 2,2-bis[methacryloxypolyethoxyphenyl]propane (2.6 E), 30 g of tetramethacryloxyethyl pyrophosphate, 0.8 g of camphorquinone, and 0.8 g of ethyl dimethylaminobenzoate, to give a liquid mixture. 10 g of this liquid mixture was mixed by kneading with 40 g of silane-treated glass powder, to give a paste. This paste was molded into test pieces suitable in size for each test, as described in the Example 1, and the compressive strength, water-leachable content, and fluoride ion release were determined.

REFERENCE EXAMPLE 1

The glass powder before silane treatment was used as a cement powder, and separately a solution of 40 g of polyacrylic acid having an average molecular weight of 30,000 in 60 g of purified water was used as a cement liquid. 1.0 g of this cement liquid was mixed by kneading with 3.0 g of the above-mentioned cement powder for 30 seconds. The resultant paste was preliminarily molded into test pieces suitable in size for each test, and allowed to set by keeping still in a thermostat at 37° C. and a relative humidity of 100% for 1 hour. With the setting test pieces, the compressive strength, water-leachable content, and fluoride ion release were determined.

REFERENCE EXAMPLE 2

3.5 g of the cement powder used in the Example 1, and 1.0 of a cement liquid prepared by dissolving homogeneously 0.4 g of camphorquinone in a solution of 20 g of 2-hydroxyethyl methacrylate and 10 g of triethyleneglycol dimethacrylate in 70 g of the cement liquid (an aqueous solution) used in the Reference Example 1 were mixed by kneading for 30 seconds. The resultant paste was preliminarily molded into test pieces of suitable size for each test, and allowed to set by keeping still in a thermostat at 37° C. and a relative humidity of 100% for 1 hour. With the test piece, the compressive strength, water-leachable content, and fluoride ion release were determined. The results obtained in the Examples and the Reference Examples are summarized in Table 2.

TABLE 2

|  | compressive strength (kg/cm$^3$) | water-leachable content (%) | fluoride ion release (ug/cm$^3$) |
| --- | --- | --- | --- |
| Example 1 | 2,580 | 0.019 | 7.52 |
| Example 2 | 2,725 | 0.015 | 7.62 |
| Example 3 | 2,850 | 0.012 | 5.80 |
| Example 4 | 3,210 | 0.009 | 5.55 |
| Reference Example 1 | 1,650 | 0.253 | 7.60 |
| Reference Example 2 | 1,830 | 0.196 | 6.15 |

The results shown in Table 2 suggest the following: The test pieces from each cement composition obtained in the Examples 1 to 4 which meets the requirements of this invention has a high compressive strength and a low disintegration rate, suggesting that the product is excellent in durability. At the same time the test piece releases much fluoride ion as a result of the use of fluoroaluminosilicate glass, which is a very excellent property as a product for dental use.

In contrast, the test piece of the Reference Example 1, where no polymerizable monomer was used and an aqueous solution of polyacrylic acid was used, is expected to exert only the effect based on the metal cross-linking, and the setting product is poor in the compressive strength with a high disintegration rate because water is used as the dispersing medium. The Reference Example 2 is an example of utilization of the reaction of a conventional aqueous polymerizable monomer for improvement of the strength, and the setting product is remarkably poorer both in the compressive strength and in the disintegration rate than those in the Examples.

[Advantages of the invention]

The invention is constituted as described above; in addition to the metal bridge formed between a carboxyl group-containing polymer and a metal chelate-forming inorganic powder, the new constitution of the practically non-aqueous system utilizing a polymerizable monomer as a reactive solvent contributes to the increase of the initial setting rate; after initial setting, the composition of this invention makes the best use of water in the oral cavity for release polyvalent metal ions from the metal chelate-forming inorganic powder so that the metal cross-linking with the carboxyl group-containing polymer proceeds, which results in marked improvement in the physical properties and durability of the set cement.

What is claimed is:

1. A method for setting a dental cement, the method comprising the steps of:

preparing in the absence of water a mixture of: (i) a polymer or co-polymer that includes an (meth)acrylic acid as an essential component of a main monomer, (ii) an inorganic powder capable of forming a metal chelate in the presence of water, and (iii) an alkyl(meth)acrylate having a hydroxyl group, wherein the polymer or co-polymer is dissolved in the alkyl(meth)acrylate having a hydroxyl group, and the inorganic powder is dispersed in the alkyl(meth)acrylate;

placing the mixture in a cavity of a tooth;

polymerizing in non-contact with water the alkyl(meth)acrylate in the mixture; and forming a metal chelate from the inorganic powder in the mixture by water in saliva.

2. The method of claim 1, wherein prior to reacting the mixture, the inorganic powder is dispersed in the solution of the polymer or co-polymer in the polymerizable monomer.

3. The method of claim 1, wherein the inorganic powder is mixed with the solution of the polymer or co-polymer in the polymerizable monomer prior to reacting.

4. The method of claim 1, wherein the weight average molecular weight of the polymer or co-polymer is 2,000 to 50,000.

5. The method of claim 1, wherein the inorganic powder comprises at least one compound selected from the group consisting of oxides, hydroxides, carbonates, phosphates, and silicates of polyvalent metals.

6. The method of claim 5, wherein the silicates are polyvalent metal ion-exuding glass.

7. The method of claim 6, wherein the polyvalent metal ion-exuding glass is fluoroaluminosilicate glass.

8. The method of claim 1, wherein the mixture further comprises a polymerization initiator for the alkyl(meth)acrylate.

9. The method of claim 1, wherein the mixture further comprises a phosphoric ester of (meth)acrylic acid.

10. The method of claim 1, wherein the mixture further comprises a (meth)acrylate and/or a carbamate which co-polymerizes with the alkyl(meth)acrylate.

11. The method of claim 1, wherein initiating comprises heating the mixture.

12. The method of claim 1, wherein initiating comprises exposing the mixture to light.

13. The method of claim 1, wherein the mixture is in the form of a paste.

14. The method of claim 1, wherein the polymer or copolymer is a homopolymer having a (meth)acrylic acid as a component, or co-polymer having, as components, a (meth)acrylic acid and a monomer having a carboxyl group.

* * * * *